(12) United States Patent
Anderson et al.

(10) Patent No.: US 8,551,079 B2
(45) Date of Patent: Oct. 8, 2013

(54) SURGICAL INSTRUMENT WITH ELECTRICAL CONNECTOR

(75) Inventors: S. Christopher Anderson, San Francisco, CA (US); Thomas G. Cooper, Menlo Park, CA (US)

(73) Assignee: Intuitive Surigical Operations, Inc., Sunnyvale, CA (US)

( * ) Notice: Subject to any disclaimer, the term of this patent is extended or adjusted under 35 U.S.C. 154(b) by 221 days.

(21) Appl. No.: 12/945,218

(22) Filed: Nov. 12, 2010

(65) Prior Publication Data

US 2011/0313405 A1    Dec. 22, 2011

Related U.S. Application Data

(60) Provisional application No. 61/356,746, filed on Jun. 21, 2010.

(51) Int. Cl.
*H01R 43/00* (2006.01)
(52) U.S. Cl.
USPC .............................. 606/1; 74/89.22; 128/898

(58) Field of Classification Search
USPC ........... 606/1; 74/89.22; 128/898; 242/157.1, 242/397.3
See application file for complete search history.

(56) References Cited

U.S. PATENT DOCUMENTS

| | | | | |
|---|---|---|---|---|
| 3,780,538 | A | * | 12/1973 | Mann ............................... 464/17 |
| 4,351,197 | A | * | 9/1982 | Carson ......................... 74/89.22 |
| 6,394,998 | B1 | | 5/2002 | Wallace et al. |
| 6,840,938 | B1 | * | 1/2005 | Morley et al. .................... 606/51 |
| 2002/0087148 | A1 | * | 7/2002 | Brock et al. ....................... 606/1 |
| 2008/0009838 | A1 | * | 1/2008 | Schena et al. ..................... 606/1 |
| 2010/0016852 | A1 | | 1/2010 | Manzo et al. |

* cited by examiner

*Primary Examiner* — Sam Yao
*Assistant Examiner* — Nathan J Jenness

(57) ABSTRACT

A surgical instrument shaft roll drive mechanism includes an electrical conductor that electrically couples the surgical instrument shaft to an electrical connector. The electrical conductor is routed adjacent to a roll drive tendon between a roll drive input capstan and a roll drive output capstan on the shaft. The electrical conductor allows an electrically conductive instrument shaft to be electrically coupled to surgical equipment for use, e.g., as a shield for electrocautery equipment.

20 Claims, 3 Drawing Sheets

SURGICAL INSTRUMENT WITH ELECTRICAL CONNECTOR

RELATED APPLICATION

This application claims the benefit under 35 U.S.C. §119 (e) of U.S. patent application Ser. No. 61/356,746 (filed Jun. 21, 2010; entitled "Surgical Instrument with Electrical Connector"), which is incorporated herein by reference.

BACKGROUND

1. Field of Invention

Aspects of this invention are related to minimally invasive surgical instruments, and more particularly to providing electrical contact to a rotating shaft in a minimally invasive surgical instrument.

2. Art

In certain circumstances, it is desirable to positively establish an electrical connection with the main instrument shaft of a minimally invasive surgical instrument. In certain electrocautery applications, such as Active Electrode Monitoring® electrocautery systems available from Encision Inc., Boulder, Colo., the instrument shaft tube is used as an electrically conductive shield. This shield is monitored for stray electrocautery energy, which may indicate that such energy may unintentionally injure the patient.

For teleoperated robotic surgical systems, instrument architectures may require that in order to roll the instrument shaft, the roll drive input be spatially displaced from the shaft by, e.g., two or more inches. And further, the instrument architectures may dictate that an electrically conductive connector for electrocautery equipment must also be spatially displaced from the instrument shaft. Various ways of establishing an electrical contact with a rolling shaft are known. What is desired, however, is a simple way of establishing an electrically conductive path between a rolling instrument shaft and an electrically conductive connector that is spatially displaced from the shaft.

SUMMARY

A minimally invasive surgical instrument includes a housing and a long instrument shaft that extends into a patient's body during surgery. The shaft is configured to roll. A capstan is coupled to the instrument shaft, and a roll drive tendon (e.g., a cable) is routed around the capstan. The roll drive tendon is also routed around a roll drive input pulley on a roll drive input shaft, so that as the roll drive input shaft rolls, the instrument shaft rolls. A separate electrical conductor, such as an electrical wire, is routed next to the roll drive tendon between the capstan on the instrument shaft and the roll drive input pulley. One end of the electrical conductor is electrically coupled to the instrument shaft, and the other end of the electrical conductor is electrically coupled to an electrical connector on the instrument. In this way, an electrical connection to the instrument shaft is made within the roll drive mechanism that permits the instrument shaft and the roll drive input shaft to each roll a relatively large amount without the need for separate and relatively more expensive components, such as slide ring connectors, on each shaft.

DETAILED DESCRIPTION

Figure 1:
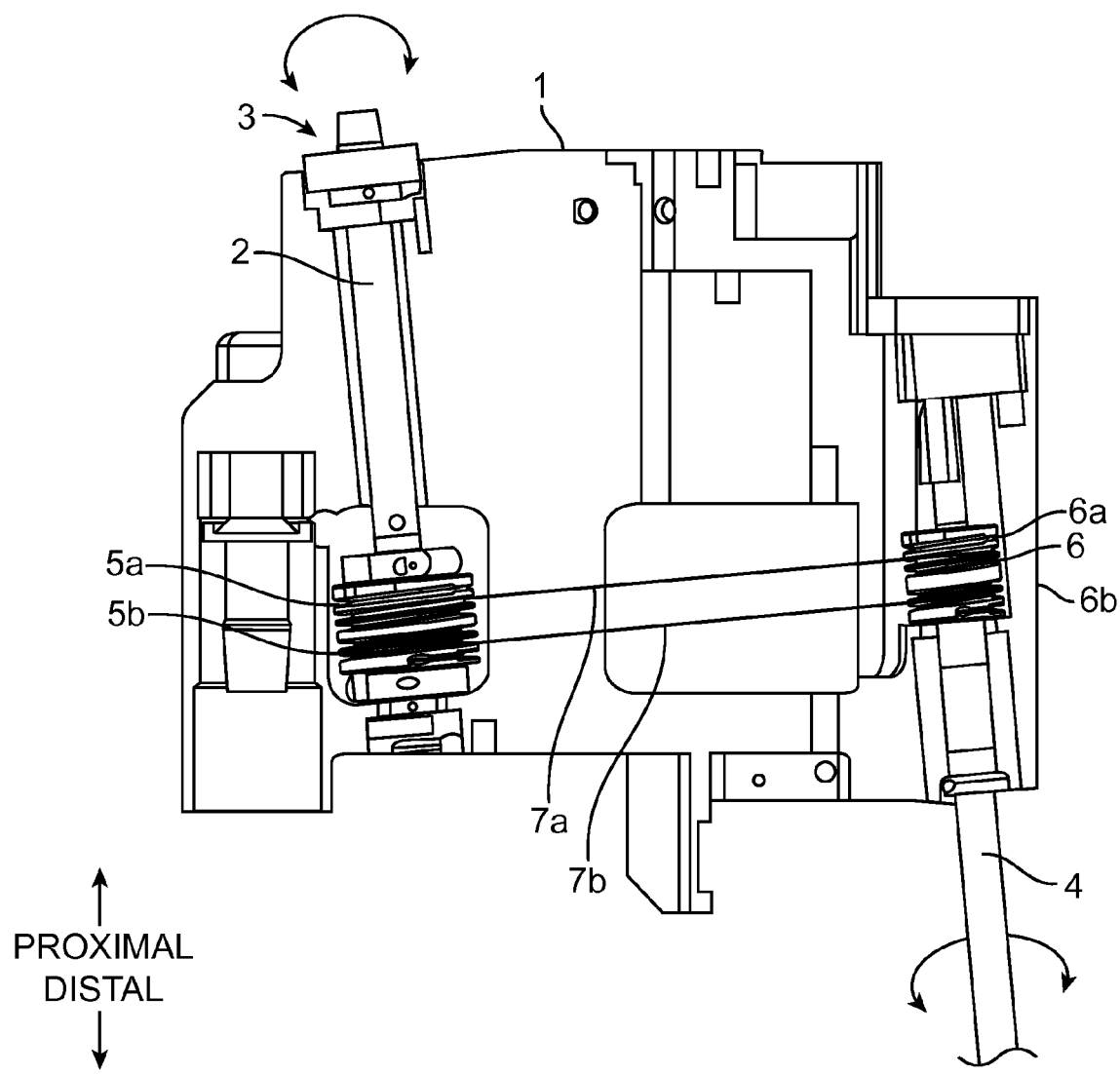
FIG. 1 is a cross-sectional side view of a portion of a surgical instrument.

This description and the accompanying drawings that illustrate inventive aspects and embodiments should not be taken as limiting—the claims define the protected invention. Various mechanical, compositional, structural, electrical, and operational changes may be made without departing from the spirit and scope of this description and the claims. In some instances, well-known circuits, structures, and techniques have not been shown or described in detail in order not to obscure the invention Like numbers in two or more figures represent the same or similar elements. Diagrammatic figures are intended to be illustrative and are not to scale.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. Mathematical and geometric terms are not necessarily intended to be used in accordance with their strict definitions unless the context of the description indicates otherwise, because a person having ordinary skill in the art would understand that, for example, a substantially similar element that functions in a substantially similar way could easily fall within the scope of a descriptive term even though the term also has a strict definition.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

FIG. 1 is a cross-sectional side view of a portion of a surgical instrument. In the illustrative depicted embodiment, the surgical instrument is designed to be coupled to a teleoperated surgical robotic manipulator assembly. Proximal and distal orientations are as shown by the arrows. As shown in FIG. 1, the surgical instrument includes a force transmission housing 1. In one embodiment, the housing is made of polyetheretherketone (PEEK). Various instrument components within the housing are omitted from the drawings to more clearly illustrate inventive aspects.

A roll input shaft 2 is mounted to roll within the housing. An input connection feature 3 at the proximal end of the roll input shaft is configured to receive an input roll torque (e.g., from a servomotor mechanism (not shown) under teleoperated control). For example, the input connection feature may be dimpled to receive small conical projections that provide a secure mechanical coupling for clockwise and counterclockwise roll torque inputs (as indicated by the depicted double-headed arrow) and that allow the instrument to be easily disengaged from the input torque mechanism. In one embodiment, the roll input shaft is made of PEEK, and the input connection feature is made of PEEK and stainless steel.

The surgical instrument includes a long shaft 4 that extends from outside the patient, though the patient's body wall, and to a surgical site within the body. The proximal end of the surgical instrument shaft is coupled (e.g., with a stainless steel roll bushing) to the housing so that the shaft can roll with reference to the housing (as indicated by the double headed arrow). The distal end of the shaft (not shown) may include various mechanisms used to assist a surgeon to perform surgery, such as wrist mechanisms, surgical end effectors, and the like. In one embodiment the instrument shaft is a stainless steel tube, so that various distal component control tendons and/or rods may be routed through the shaft to control distal component movements. In one embodiment, tension on these distal component control tendons keeps the shaft in place in the housing and helps to insure a good electrical connection between the shaft and the capstan.

FIG. 1 also shows two roll drive input capstans 5a,5b coupled to roll input shaft 2. In the illustrative depicted embodiment, the separate drive capstans are individually connected to the roll input shaft via screws and a collar. In other aspects, a single element with two capstan features may be used (e.g., similar to the roll drive output capstan described below), and various connections to the shaft may be used. The screws and collar in the depicted embodiment allow roll drive tendons that are routed around the capstans (described below) to be placed in tension by rotating and securing the capstans on the shaft. In the depicted embodiment, the two roll drive input capstans have helical grooves, although other groove configurations may be used. In one embodiment, the drive input capstans are anodized aluminum.

As shown in FIG. 1, a single roll drive output capstan 6 is coupled to the instrument shaft as shown. The output capstan includes two capstan features 6a,6b. As depicted, each capstan feature includes a helical groove, although other groove configurations may be used. In one embodiment, the output capstan is stainless steel with gold plating.

In order to transmit roll torque from the roll input shaft to the instrument shaft (and alternatively, to transmit the shaft's reactive torque to the roll input shaft), two roll drive tendons 7a,7b are coupled between the roll drive input capstans and the roll drive output capstan. In one embodiment the roll drive tendons are tungsten cables that are secured to the input and output capstans with swaged or crimped ends in sockets.

As shown in FIG. 1, the first roll drive tendon 7a is routed between roll drive input capstan 5a and roll drive output capstan feature 6a, and the second roll drive tendon 7b is routed between roll drive input capstan 5b and roll drive output capstan feature 6b. Along the length of the first tendon 7a, it wraps around the input capstan 5a in a first direction (e.g., clockwise when viewed from the proximal end of the roll input drive shaft) and around the output capstan feature 6a in a second direction (e.g., counterclockwise). Similarly, along the length of the second tendon 7b, it wraps around the input capstan 5b in the second direction and around the output capstan feature 6b in the first direction. Thus when viewed from the proximal end of the surgical instrument, the cables cross over each other to form a "figure 8". This configuration allows positive transfer for roll and reactive torques in both roll directions when the drive tendons are placed in tension as described above. The crossing also provides additional space within the housing, which would not be available if the tendons were not crossed, for other mechanisms (not shown) inside the housing. Alternatively, the drive tendons may be routed so that they do not cross, and the ends of each tendon wrap in the same direction around the input and output capstans. This alternative configuration also allows positive transfer for roll and reactive torques in both roll directions when the drive tendons are placed in tension.

Figure 2:
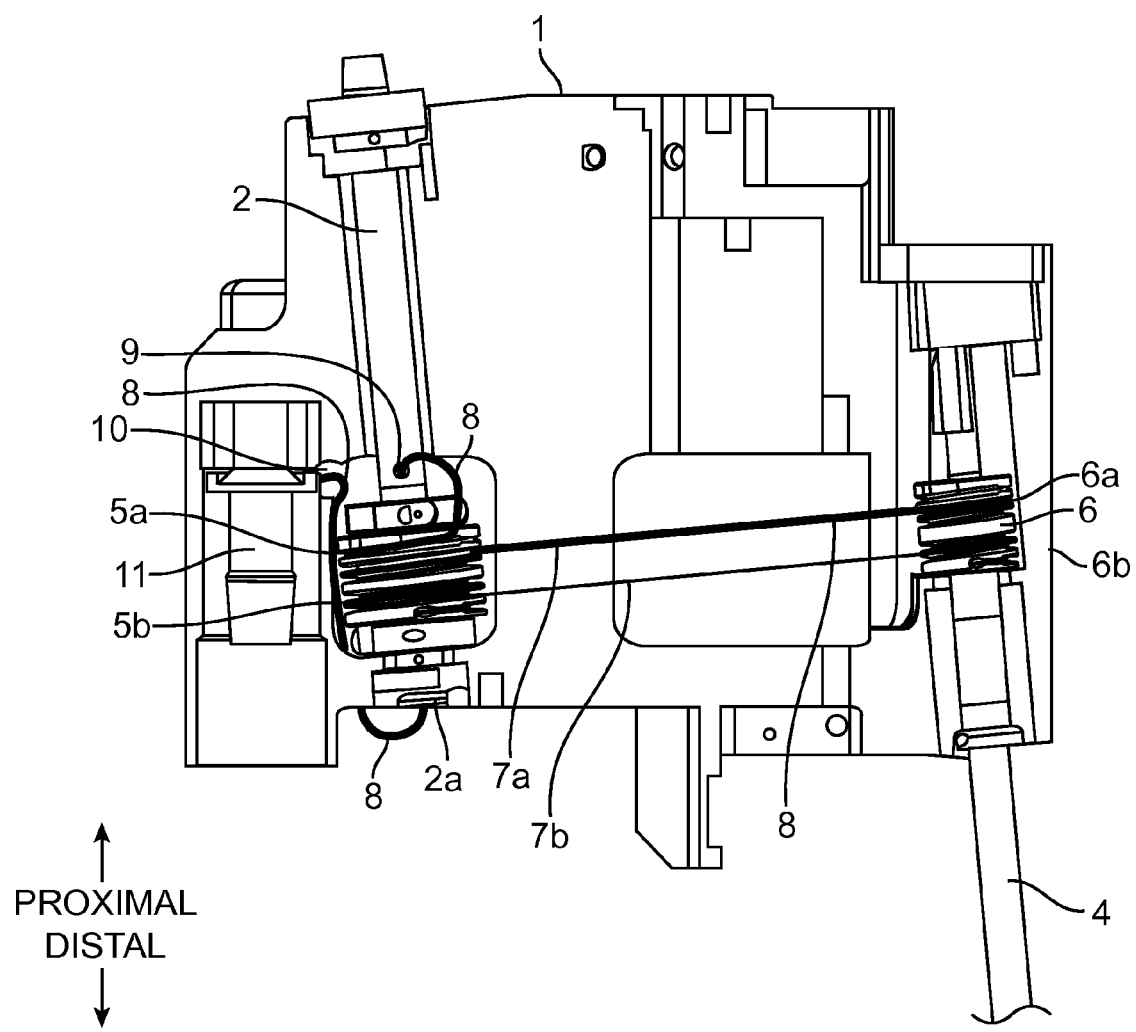
FIG. 2 is a cross-sectional side view of the portion of the surgical instrument as shown in FIG. 1 that further includes an electrical connector.

FIG. 2 is a cross-sectional side view of the portion of the surgical instrument as shown in FIG. 1 that further includes an electrical connector in accordance with aspects of the invention. In accordance with an aspect of the invention, an electrical conductor (e.g., an insulated wire) is routed alongside/adjacent one of the roll drive tendons between the roll drive input shaft and the instrument shaft. As shown in the illustrative embodiment in FIG. 2, electrical wire 8 is routed adjacent to roll drive tendon 7a.

One end 8a of electrical wire 8 is soldered to the roll drive output capstan 6 so that an electrical connection is established between the wire and the instrument shaft 4. The wire is routed around output capstan feature 6a in the same groove as, and outside of, tendon 7a. Wire 8 is then routed adjacent tendon 7a between the roll drive output and input capstans and wraps around input capstan 5a in the same groove as, and outside of tendon 7a (described in more detail below). Wire 8 is then routed off of roll drive input capstan 5a and through a small hole 9 into the hollow interior of roll input drive shaft 2. Wire 8 then travels through the center of roll input drive shaft, where it can freely rotate, to exit the distal end 2a of the drive shaft. Alternately, the wire could be coiled to wind and unwind around the shaft. After wire 8 exits the drive shaft, it is routed through a small hole 10 in housing 1, and the other end 8b of wire 8 is soldered to the outside electrically conductive element of electrical connector (plug) 11, which is mounted in housing 1. The wire is not under tension between the roll drive input and output capstans, although in general slack is removed from the wire between the capstans. Sufficient slack is left in the wire between the input pulley and drive shaft and between the drive shaft and the plug to allow the drive shaft to roll with full range of motion without placing undue stress on the wire.

In one embodiment, plug 11 is gold plated stainless steel and is compatible with Active Electrode Monitoring® electrocautery systems available from Encision Inc., Boulder, Colo. The electrocautery system is coupled to the plug so that active electrocautery energy is routed to the instrument's electrocautery end effector via the plug's centerline connector, and the system's stray energy monitoring capability is coupled to the plug's outer connector. Thus, if the surgical instrument is an electrocautery instrument that uses instrument shaft 4 as a shield for stray currents from the active electrocautery electrode, wire 8 conducts these stray currents from the instrument shaft to the plug. In turn, the stray currents may then be monitored by the electrocautery system for patient safety.

Figure 3:
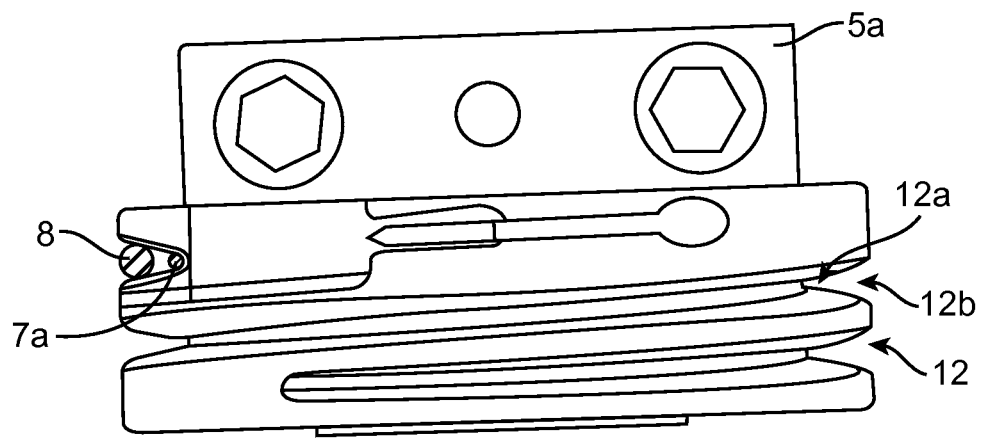
FIG. 3 is a side view of a roll drive input capstan.

FIG. 3 is a side view of roll drive input capstan 5a in more detail. In accordance with an aspect of the invention, the helical capstan groove 12 is configured with an inner radius groove 12a and an outer radius groove 12b. The width of inner radius groove is smaller than the width of the outer radius groove, so that the single capstan groove 12 guides both a relatively smaller radius tendon/cable/wire/line/etc. feature in the inner groove and a relatively larger radius tendon/cable/wire/line/etc. feature in the outer groove without the two guided features contacting one another in the groove. As shown in FIG. 3, for example, roll drive tendon 7a is routed in groove 12's inner radius groove, and electrical wire 8 is routed in groove 12's outer radius groove, so that the tendon and the electrical wire can be driven at different pulley ratios at the input to keep their lengths consistent between the input and output. The collar and screws used to secure the roll drive input capstan to the roll drive input shaft once proper tension is applied to the drive tendon are also visible in FIG. 3, as is a detent that is used to allow space for a way of securing the wire to the capstan, as described below.

Figure 4:
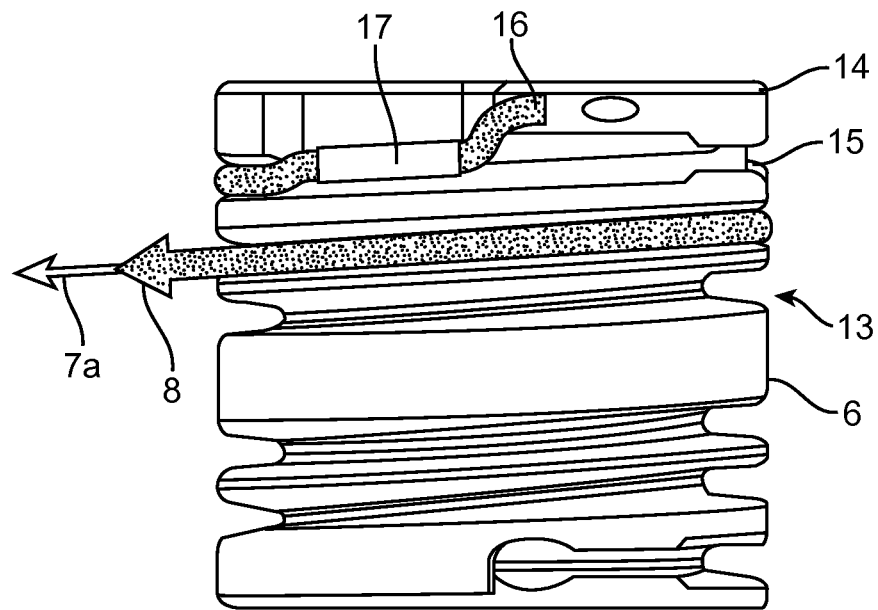
FIG. 4 is a side view of a roll drive output capstan.

FIG. 4 is a side view of roll drive output capstan 6 in more detail. As shown in FIG. 4, roll drive tendon 7a is routed in helical pulley groove 13 around roll drive output capstan section 6a, and electrical wire 8 is laid over the roll drive tendon in the groove. It can be seen that since the input and output drive capstans have different radii, the separate inner and outer grooves in the roll drive input capstan described above maintain the payin/payout ratio between the drive tendon and the wire. The drive tendon terminates in the output capstan at a swage/crimp 14 held securely in a counterbore socket 15 (a similar technique is used to anchor the drive tendon in the input capstan). Electrical wire 8 terminates at the output capstan with an electrically conductive solder connection 16 to the capstan. In one illustrative embodiment, wire 8 is mated near the end of the drive tendon by using a shrink wrap tube (e.g., fluorinated ethylene propylene (FEP)) 17. A similar mating is used at the roll drive input capstan, so that the wire is mated to both ends of the drive tendon.

We claim:

1. A surgical instrument comprising:
    a roll drive input shaft and a roll drive input capstan on the roll drive input shaft;
    an instrument shaft, an end effector disposed at a distal end of the instrument shaft, and a roll drive output capstan on the instrument shaft;
    a roll drive tendon routed around the roll drive input capstan and around the roll drive output capstan, wherein the roll drive input capstan, the roll drive tendon, and the roll drive output capstan are operably coupled to roll the instrument shaft about a longitudinal axis of the instrument shaft;
    an electrical connector; and
    an electrical conductor separate from the roll drive tendon;
    wherein a first end of the electrical conductor is electrically coupled to the electrical connector, wherein the electrical conductor is routed around the roll drive input capstan and around the roll drive output capstan, and wherein a second end of the electrical conductor is electrically coupled to the instrument shaft.

2. The instrument of claim 1:
    wherein the electrical conductor is adjacent the roll drive tendon around at least a portion of the roll drive input capstan, between the roll drive input capstan and the roll drive output capstan, and around at least a portion of the roll drive output capstan.

3. The instrument of claim 2:
    wherein the roll drive tendon and the electrical conductor are routed around the roll drive input capstan in a first direction and around the roll drive output capstan in a second direction that is opposite to the first direction.

4. The instrument of claim 1:
    wherein the roll drive input capstan comprises a groove; and
    wherein the roll drive tendon is routed in an inner radius portion of the groove and the electrical conductor is routed in an outer radius portion of the groove.

5. The instrument of claim 4:
    wherein the groove is defined in the roll drive input capstan as a helical shape.

6. The instrument of claim 4:
    wherein the inner radius portion of the groove has a smaller width than the outer radius portion of the groove.

7. The instrument of claim 1:
    wherein the roll drive output capstan comprises a groove; and
    wherein the roll drive tendon is routed in an inner radius portion of the groove and the electrical conductor is routed in an outer radius portion of the groove.

8. The instrument of claim 7:
    wherein the groove is defined in the roll drive output capstan as a helical shape.

9. The instrument of claim 7:
    wherein the inner radius portion of the groove has a smaller width than the outer radius portion of the groove.

10. The instrument of claim 1 further comprising:
    a second roll drive tendon routed around the roll drive input capstan and around the roll drive output capstan;
    wherein the roll drive tendon and the second roll drive tendon are routed around the roll drive input capstan in opposite directions and around the roll drive output capstan in opposite directions.

11. The instrument of claim 1:
    wherein the electrical conductor comprises an insulated wire.

12. The instrument of claim 1:
    wherein the roll drive input shaft comprises a hollow interior, a hole into the hollow interior through a side of the roll drive input shaft, and an exit from the hollow interior at an end of the roll drive input shaft; and
    wherein the electrical conductor is routed from the electrical connector, through the exit from the hollow interior, through the hollow interior, and through the hole into the hollow interior to the roll drive input capstan.

13. The instrument of claim 1:
    wherein the electrical conductor is slack between the roll drive input capstan and the roll drive output capstan.

14. The instrument of claim 1:
    wherein the instrument shaft is configured to act as a shield for stray currents from an active electrocautery electrode.

15. The instrument of claim 1:
    wherein the output capstan at a proximal end of the instrument shaft.

16. A method of making a surgical instrument, comprising the acts of:
    positioning a roll drive input capstan on a roll drive input shaft;
    positioning a roll drive output capstan on a shaft of the instrument, the instrument having an end effector at a distal end of the shaft of the instrument;
    routing a roll drive tendon around the roll drive input capstan and around the roll drive output capstan, wherein the roll drive input capstan, the roll drive tendon, and the roll drive output capstan are operably coupled to roll the instrument shaft about a longitudinal axis of the instrument shaft;

electrically coupling a first end of an electrical conductor to an electrical connector on the surgical instrument, wherein the electrical conductor and the roll drive tendon are separate from one another;

routing the electrical conductor around the roll drive input capstan and around the roll drive output capstan; and electrically coupling a second end of the electrical conductor to the instrument shaft.

17. The method of claim 16 further comprising:
routing the electrical conductor adjacent the roll drive tendon around at least a portion of the roll drive input capstan, between the roll drive input pulley and the roll drive output capstan, and around at least a portion of the roll drive output capstan.

18. The method of claim 17 further comprising:
routing the roll drive tendon and the electrical conductor around the roll drive input capstan in a first direction and around the roll drive output capstan in a second direction that is opposite to the first direction.

19. The method of claim 16 further comprising:
forming a groove in the roll drive input capstan, wherein the groove comprises a relatively smaller width inner radius groove and a relatively larger width outer radius groove;
routing the roll drive tendon in the inner radius groove; and
routing the electrical conductor in the outer radius groove.

20. The method of claim 19 further comprising:
forming the groove helical shape.

* * * * *